United States Patent [19]

Nakamura et al.

[11] Patent Number: 5,624,436
[45] Date of Patent: Apr. 29, 1997

[54] LASER BEAM AND ABLATING APPARATUS AND RELATED METHOD

[75] Inventors: Takua Nakamura, Aichi; Kazuharu Sugiyama, Anjo, both of Japan

[73] Assignee: Nidek Co., Ltd., Gamagori, Japan

[21] Appl. No.: 187,735

[22] Filed: Jan. 28, 1994

[30] Foreign Application Priority Data

Jan. 29, 1993 [JP] Japan ................... 5-034061

[51] Int. Cl.$^6$ ................... A61H 5/02
[52] U.S. Cl. ................... 606/12; 606/3; 606/5; 606/10; 219/121.73; 219/121.8
[58] Field of Search ................... 219/121.6, 121.73, 219/121.74, 121.75, 121.8; 606/2, 3, 5, 10–19

[56] References Cited

U.S. PATENT DOCUMENTS

| | | | |
|---|---|---|---|
| 4,653,495 | 3/1987 | Nanaumi ................... | 606/9 |
| 4,721,379 | 1/1988 | L'Esperance ................... | 606/5 |
| 4,941,093 | 7/1990 | Marshall et al. ................... | 606/5 |

FOREIGN PATENT DOCUMENTS 9222255  12/1992  WIPO ................... 606/4

OTHER PUBLICATIONS

"Photoablative reprofiling of the cornea using an excimer laser: Photorefractive Keratectomy" by Marshall et al; Lasers in Ophthalmology vol. 1, No. 1 pp. 21–48, 1986.

*Primary Examiner*—David M. Shay
*Attorney, Agent, or Firm*—Finnegan, Henderson, Farabow, Garrett and Dunner, L.L.P.

[57] ABSTRACT

An ablation apparatus for ablating by laser beam including a laser beam providing means for providing laser beam to ablate an object to be processed into a desired form, a light beam delivering optical system for delivering the laser beam to the object to be processed, an ablation area changing diaphragm for changing ablation area on the object to be processed, and a control device for controlling the motion of the ablation area changing diaphragm, the ablation apparatus comprising instructing device for instructing the controlling device to form a curved surface with a first optical characteristic on the rate reference object which has a known ablation rate as to an ablation rate of the object to be processed, measuring device for measuring a second optical characteristic of the curved surface actually formed on a rate reference object in accordance with control by the controlling device, input device for inputting the second optical characteristic measured by the measuring device, and correcting device for calculating an ablation rate with respect to the object to be processed based on a comparison between the second optical characteristic input by the input device and the first optical characteristic whereby a driving information of the ablation apparatus is corrected.

23 Claims, 7 Drawing Sheets

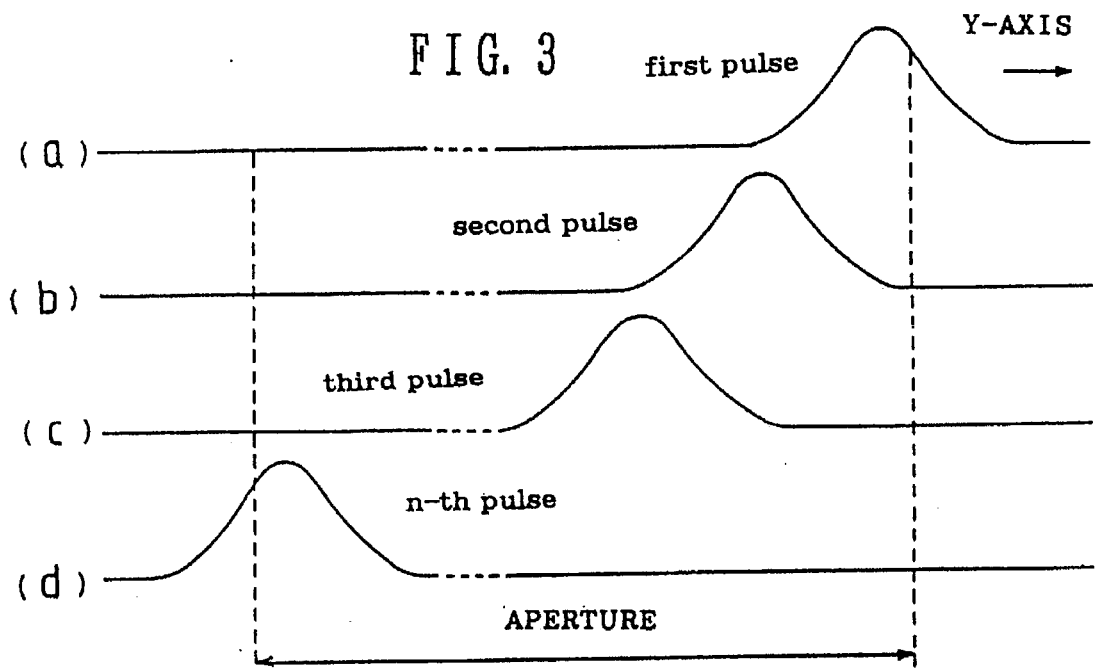
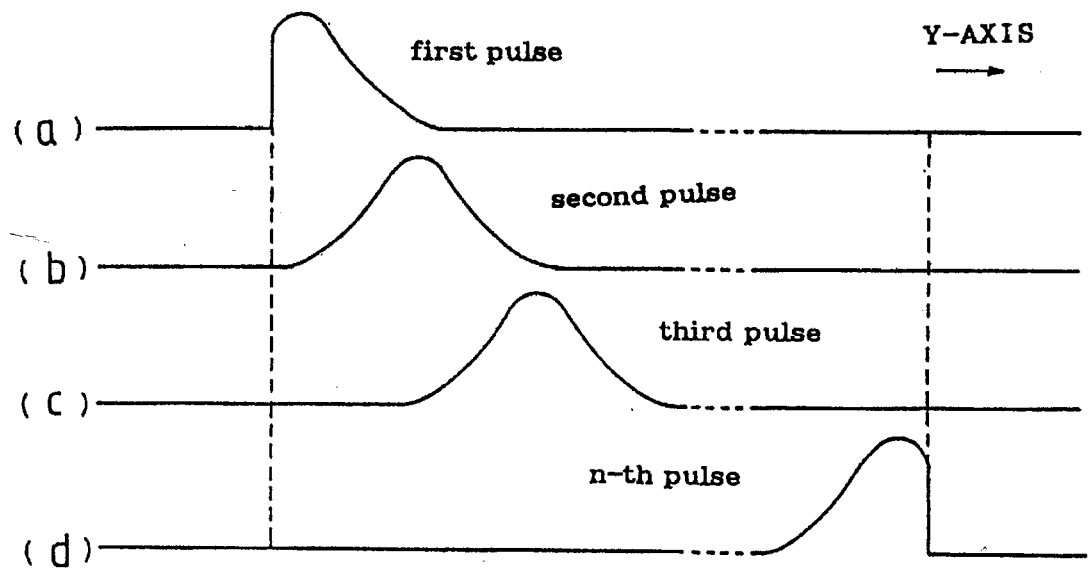

LASER BEAM AND ABLATING APPARATUS AND RELATED METHOD

BACKGROUND OF THE INVENTION

1. Field of the Invention

The present invention relates to an apparatus for ablating an object by laser beam and an ablating method using the ablation apparatus, and more particularly to an apparatus for ablating the surface of a cornea by laser beam to correct the refractive power and an ablating method thereof.

2. Description of Related Art

There are conventionally known processing apparatuses for ablating an object by laser beam. A laser beam used mainly for fine processing, is the excimer laser, particularly argon fluoride (ArF) laser with a wavelength 193 nm. The use of high harmonic wave, such as Nd:YAG laser, and others have also been tried. A known fine processing apparatus is an apparatus for ablating a surface of the cornea of an eye to change curvature thereof and thereby correct a refractive error of the eye. In such ablating apparatus, it is important to control the ablating operation so that the ablated area is uniform in depth.

Therefore, various ablating methods to ablate an object uniformly in depth are proposed. In Japanese Patent Application No. 2-416767 corresponding to U.S. patent application Ser. No. 07/812,819, the inventor of the present invention also has proposed an ablating apparatus, that is, an apparatus for ablating a surface of a cornea by excimer laser beam having a uniform intensity distribution in one direction and a Gaussian distribution in a vertical direction thereof, and scanning optical elements in the Gaussian direction, so that the ablated area is uniform in depth.

In one constructed apparatus for ablating a surface of a cornea with uniform depth, the laser beam irradiating area on a cornea is restricted by a variable aperture and a variable width parallel slit, and the irradiating area is controlled to form a cornea shape with a desired curvature, to correct refractive error of the cornea including myopia, astigmatism and others.

However, ablating depth per pulse (per scan in a method described below in the embodiment) subtly varies according to primary factors such as kinds of objects to be ablated, output energy of the laser beam and other processing conditions. The ablating depth per one scan of the laser beam is hereinafter called "ablation rate" in the present specification. It may be considered that the ablation rate by excimer laser is substantially the same when the laser is continuously worked, but the ablation rate often changes when processing conditions are different, even if the output energy of the laser beam is the same. Such change of ablation Pate is fatal to a processing apparatus which needs close control of ablating depth, particular in an apparatus for forming a cornea into a desired regular shape. Due to a changed ablation rate, the cornea is formed into a shape different from the desired one.

It is generally difficult to measure the ablation rate, in particular the ablation rate of a transparent object such as a cornea.

Even if the measurement of the ablation rate itself can be conducted, by an electron microscope and the like, measuring the ablation rate every ablation is troublesome in operation thereof and too expensive.

SUMMARY OF THE INVENTION

The present invention has been made in view of the above circumstances and has an object to overcome the above problems and to provide an apparatus for ablating by laser beam and an ablating method using the apparatus, capable of easily correcting change of the ablation rate.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ablation apparatus of this invention for ablating by a laser beam of this invention including a laser beam providing a means for providing laser beam to ablate an object to be processed into a desired form, a light beam delivering optical system for delivering the laser beam to the object to be processed, an ablation area changing means for changing the ablation area on the object to be processed, and a control means for controlling the motion of the ablation area changing the means, comprises instructing means for instructing the controlling means to form a curved surface with a first optical characteristic on a rate reference object which has a known ablation rate against the ablation rate of the object to be processed, measuring means for measuring a second optical characteristic of the curved surface actually formed on the rate reference object in accordance with control by the controlling means, input means for inputting the second optical characteristic measured by the measuring means, and correcting means for calculating an ablation rate to the object to be processed based on a comparison between the second optical characteristic input by the input means and the first optical characteristic, whereby a driving information of the ablation apparatus is corrected.

In the a second aspect of the present invention, a cornea operating apparatus for irradiating an eye to be operated by a laser beam to correct the refractive error of the eye comprises a laser source for emitting a laser beam having a Gaussian distribution in a direction of beam section, an ablation optical system for irradiating the laser beam emitted from the laser source onto a surface of the cornea of the eye to be operated, scanning means (translational scanning means) for scanning the laser beam in the direction of Gaussian distribution, which is disposed on the ablation optical system, ablation changing rate input means for inputting the change rate between the refractive power of a simulated lens and a predetermined reference refractive power, the simulated lens being produced by disposing an ablation reference object in the ablation optical system which is ablated instead of the cornea, and driving control means for controlling the output power of the laser beam emitted from the laser source and the scanning condition of the laser beam to be scanned by the scanning means, based on the change rate of the ablation rate input by the input means.

In a third aspect of the present invention, an ablating method for ablating an object to be processed into a desired shape by laser beam, while changing an ablation area, includes the following processes; a rate comparison object disposing process for disposing a rate comparison object in the optical path of the laser beam, the rate comparison object having a known ablation rate as to the ablation rate of the object to be processed, an ablation plume removing process for removing ablation plume produced from the rate reference object while irradiated by the laser beam in order to maintain the stability of ablation, a process for controlling to form a curved surface on the rate reference object so that the curved surface has a first optical characteristic, a measuring process for measuring a second optical characteristic of the curved surface actually formed on the rate reference object, an input process for inputting the second optical characteristic measured by the measuring process, a calculating process for calculating the ablation rate to be applied to the object to be processed based on a comparison between the second optical characteristic input by the input process and the first optical characteristic, and a processing process for processing the object to be processed based on the ablation rate calculated by the calculating process.

According to the present invention, the current ablation rate of the laser can be easily found, therefore, processing an object can be exactly conducted by using the ablation rate as a correct data.

The change of the ablation rate can be obtained as a change of rate for the refractive power, therefore it has a direct influence on forming the curved surface to correct the refraction of cornea.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

FIGS. 3(a) through 3(d) are diagrams showing the laser beam intensity profile in the vertical (Y-axis) direction on an diaphragm;

FIGS. 4 (a) through 4(d) are diagrams showing the laser beam intensity profile in the vertical (Y-axis) direction on the cornea of an eye;

DETAILED DESCRIPTION OF THE PREFERRED EMBODIMENTS

A detailed description of one preferred embodiment of an apparatus for ablating by laser beam and an ablating method utilizing the apparatus embodying the present invention will now be given referring to the accompanying drawings.

Figure 1:
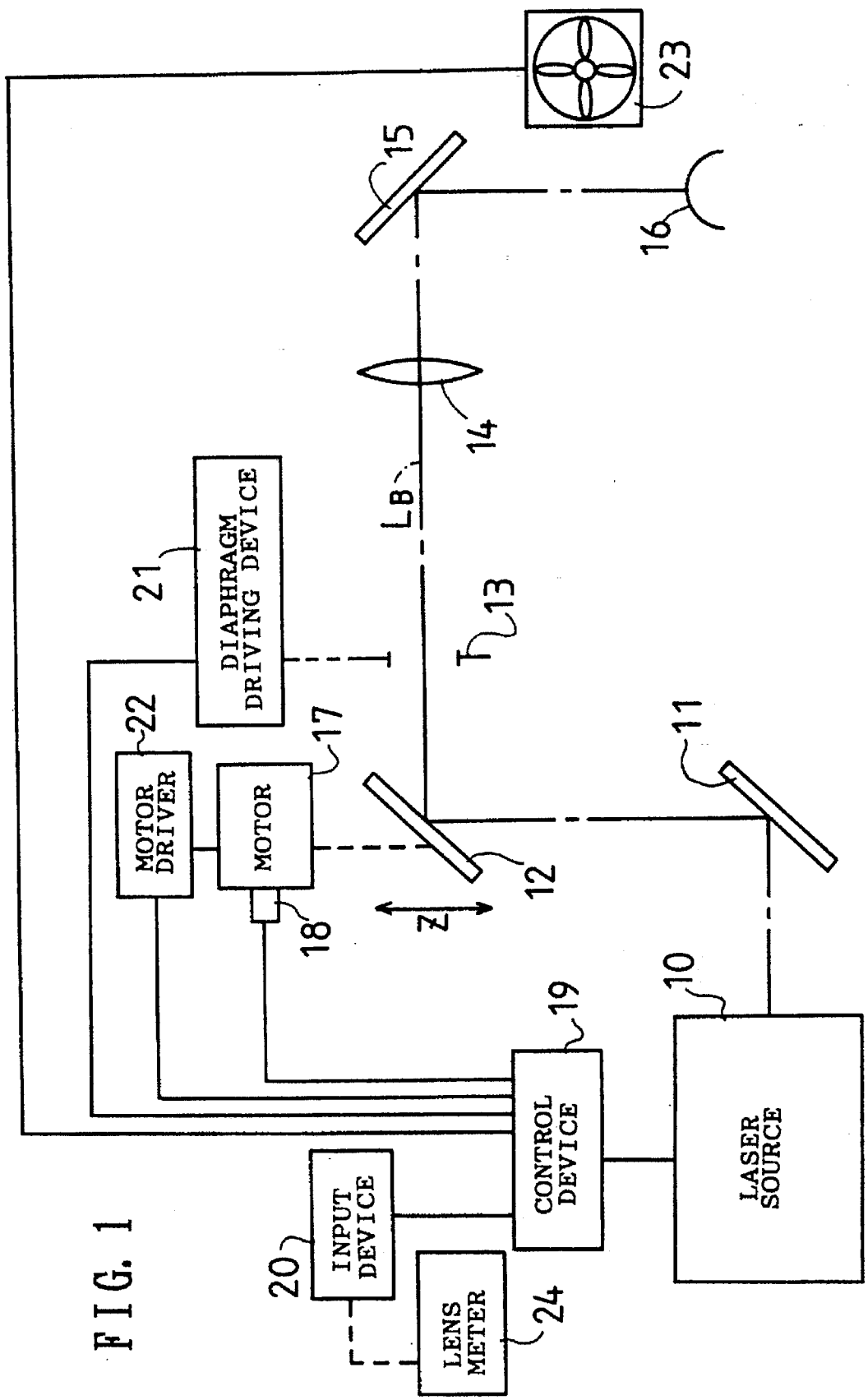
FIG. 1 is a schematic diagram of the arrangement of optical components of the first embodiment in accordance with the present invention.

In FIG. 1, shown is a substantial construction of an optical system of an ablation apparatus for cornea in an embodiment according to the present invention. The optical system is applied with an ablation apparatus disclosed by the present inventor in Japanese Patent Application No. HEI 2-416767 which corresponds to U.S. patent application Ser. No. 07/812,819.

Specifically, an optical system of the ablation apparatus includes a laser source 10 (preferably an excimer laser), plane mirrors 11, 12, 15 for reflecting the laser beam LB emerging from the laser source 10, a diaphragm 13 with a variable diameter located in the optical path between the mirrors 12, 15, and a projection lens 14 for projecting the laser beam LB passing through the diaphragm 13 to a cornea 16 via mirror 15.

The laser beam LB emerging from the laser source 10 is reflected 90° by the plane mirror 11 and another 90° by the mirror 12 while it remains in the same plane. After the laser beam passes through the diaphragm 13, the laser beam LB is also reflected 90° by the plane mirror 15 in the same plane, and projected to the surface of the cornea 16.

The projection lens 14 is conjugated with the diaphragm 13 and the cornea 16, and the laser beam passing through the aperture defined by the diaphragm 13 in a confined space, is projected on the surface of the cornea 16 such that an ablation area of the cornea is restricted.

The cornea is placed at a position having a predetermined positioning in relation to the apparatus.

Figure 2:
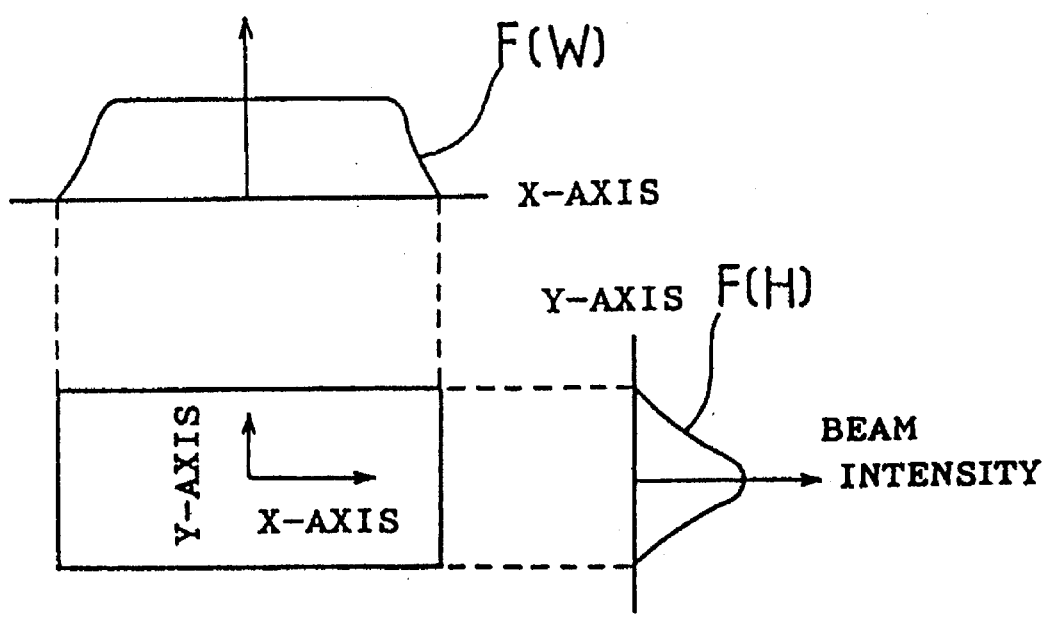
FIG. 2 is a schematic diagram of a horizontal (X-axis) beam intensity profile and a vertical (Y-axis) beam intensity of a laser beam from an excimer laser as used in the embodiment of FIG. 1.

The beam section profile of the laser beam emitted from the laser source 10 of FIG. 1, has an almost uniform intensity distribution F(W) in the horizontal direction (X-axis direction) of the laser beam, but the beam intensity distribution in the vertical direction (Y-axis direction) is a Gaussian distribution F(H) as shown in FIG. 2.

The plane mirror 12 of FIG. 1 is movable parallel to the Z-axis by a driving motor 17, and the position of the mirror 12 (amount of movement) is detected by a positioning detector 18. The positioning detector 18 may comprise, for example, a rotary encoder attached to a driving axis of the mirror's driving motor 17.

The positioning detector 18 and the laser source 10 are connected to a control device 19, and the laser pulses are emitted based on output signal from the positioning detector 18. The operation of the present apparatus is controlled by a microcomputer of the control device 19.

That is, an input device 20 is connected to the control device 19 and, via the input device 20, input are data including the radius of curvature of the pre-ablation cornea, correction power of an eye, size of the optical zone and the transition zone which is the boundary area between the ablation area (exactly optical zone) and the non-ablation area, the width of the transition zone and the depth of the ablation to be taken place or the like.

And also, a diaphragm driving device 21 for changing a diameter of the diaphragm 13 is connected to the control device 19, and the diameter of the diaphragm 13 is changed based on an output signal from the control device 19. Numeral 22, in FIG. 1, is a motor driver connected to the motor 17, so that the motor driver 22 drives the motor 17 based on an output signal from the control device 19. Numeral 23 is an air blower for removing ablation plume to be produced at the time of making simulated lens by ablating an ablation rate reference object, which is connected to the control device 19. Numeral 24 is a lensmeter for measuring the refractive power of spectacle lens. The refractive power of a transparent plate 25 after ablated is measured by the lensmeter 24, and the measured refractive power is input to the control device 19 through the input device 20 by an operator. The measured refractive power may be also automatically input to the control device 19 by switch operation.

For the lensmeter, various known lensmeters may be utilized, for instance, "LENS METER LM-100" produced by the present applicant and others, the detail explanation is therefore omitted here.

As described above, the mirror 12 moves parallel to the Z-axis direction of FIG. 1, whereby the laser beam is moved in parallel in the direction of the Gaussian distribution. The plane mirror 12 moves synchronously to the laser pulse output by laser source 10, and after one or more laser pulses have been output at a certified position of the plane mirror 12, the mirror 12 moves to a next position, and again at that position of the mirror 12 one or more laser pulses will be further output as the mirror 12 moves further to a next position. This moving operation is repeated from the one end of the diaphragm 13 to the other end. This means that the irradiation of the laser beam is repeated on the ablation area of the cornea 16 at a determined interval (by one or more of the laser pulses) so that the pulses are combined and a uniform depth of ablation is achieved.

The amount of movement of the plane mirror 12 is determined by correlation among several components, e.g., the depth of ablation, the degree of uniformity required or the intensity and intensity distribution of the laser beam and the like. The adjustment of the laser beam's intensity or the ablation's depth per one pulse may be obtained by adjusting the output energy of the laser source within a certain range.

For convenience of explanation, it may be assumed that the plane mirror 12 moves for every pulse although such a one-to-one relationship is not required for the present invention. FIGS. 3(a) through 3(d) show the change of the intensity distribution of the laser beam in Y-axis direction on the diaphragm 13. FIGS. 4(a) through 4(d) show the change of the intensity distribution in the Y-axis direction on the cornea 16. FIGS. 5(a) through 5(e) show the ablation on the cornea.

Figure 5:
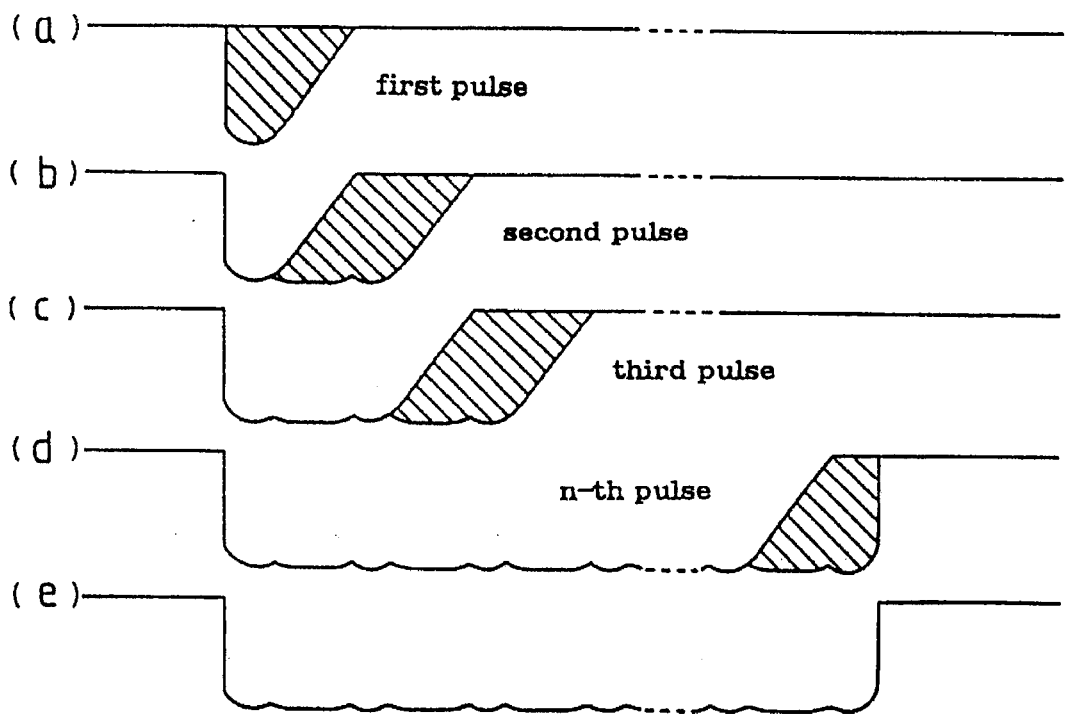
FIGS. 5(a) through 5(e) are diagrams to explain the condition (process) of ablation of FIG. 4.

When a first pulse of the laser beam having the intensity distribution shown in FIG. 3(a) on the diaphragm 13 is irradiated on the cornea 16 by the projection lens 14, the intensity distribution on the cornea 16 is as shown in FIG. 4(a). At that time, the cornea 16 is ablated by the irradiation of the laser beam, as shown with oblique lines in FIG. 5(a). When a second pulse of the laser beam is irradiated, as the plane mirror 12 has been moved in the Z-axis direction, the intensity distribution on the diaphragm 13 is changed as shown in FIG. 3(b). Accordingly, the intensity distribution projected on the cornea 16 by the projection lens 14 is as shown in FIG. 4(b), and the cornea 16 is further ablated as shown with oblique lines in FIG. 5(b). The third pulse of the laser beam produces an intensity distribution on the diaphragm 13 as shown in FIG. 3(c) and the intensity distribution on the cornea 16 as shown in FIG. 4(c), whereby the area of the cornea shown with oblique lines in FIG. 5(c) is further ablated. Similarly, the fourth and the subsequent laser pulses up to the n-th pulse of the laser beam, cause an intensity distribution on the diaphragm 13 as shown in FIG. 3(d). FIG. 4(d) shows the intensity distribution on the cornea 16 and the area shown in FIG. 5(d) with oblique lines is ablated.

By moving the plane mirror 12 in parallel to the Z-axis direction synchronously with respect to the laser pulse and irradiating the laser beam while scanning it in the direction of its non-uniform intensity distribution, the cornea 16 is ablated with an almost uniform depth shown in FIG. 5(e).

As proposed in Japanese Patent Application No. HEI 4-286999 entitled: Ablation Apparatus by Laser-Beam by the applicant of the present invention, the positioning of an image-rotator on the optical path and by rotating the direction of the beam, the problem of the dispersion of the intensity distribution by the lack of adjustment of a laser resonator, is solved.

Figure 6:
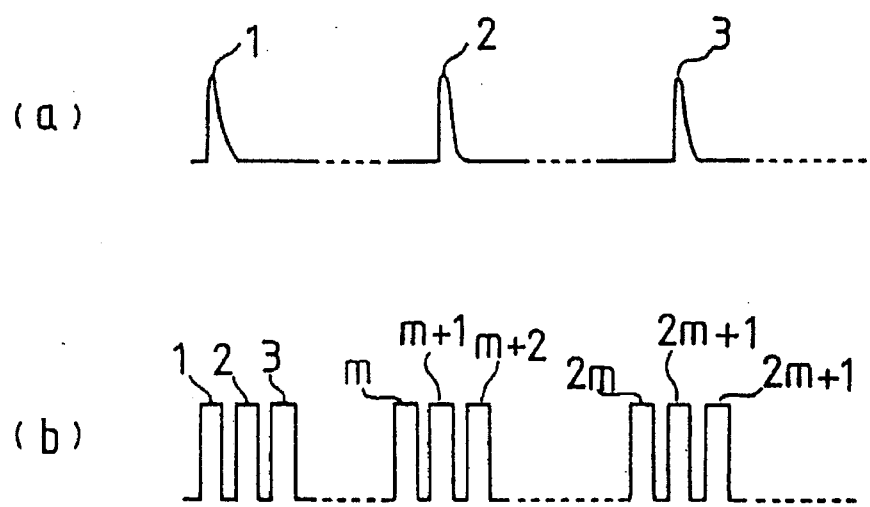
FIGS. 6(a) and 6(b) are timing charts to explain the movement control of the plane mirror 12 shown in FIG. 1 with respect to the laser pulse.

FIGS. 6(a) and 6(b) are timing charts to explain the timing of a control mechanism that moves the plane mirror 12 synchronously with respect to the laser pulses. In the FIG. 6(a), the output pulse of the laser beam is shown; and FIG. 6(b) shows output signals from the detector 18 detecting the position of the plane mirror 12.

Although, in the above embodiment a ship of the direction of the laser beam's energy distribution is described, other directions may be employed.

Figure 9:
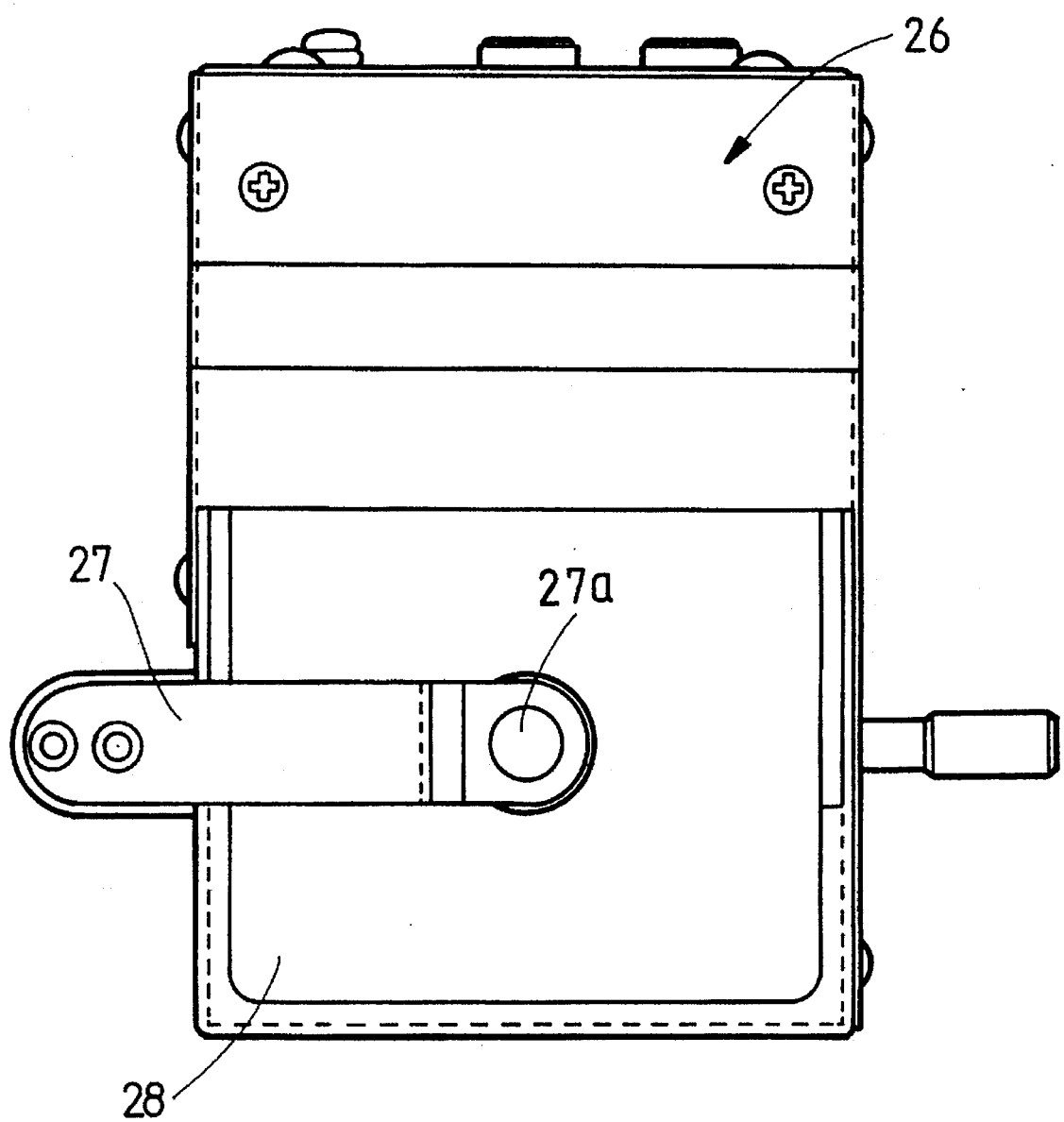
FIG. 9 is a schematic exterior plane view of an air blower device,or removing ablation plume.
Figure 10:
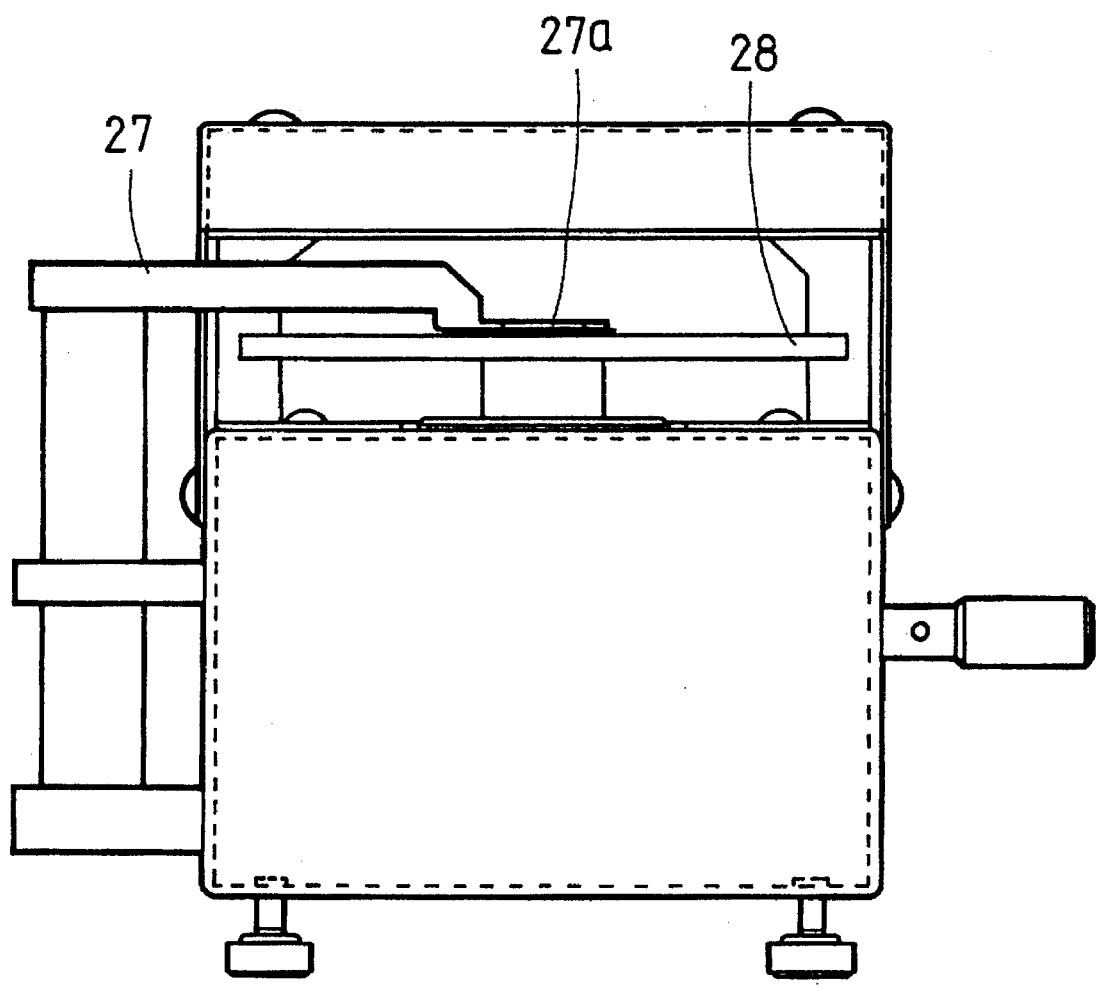
FIG. 10 is a schematic exterior side view of an air blower device shown in FIG. 9.

FIGS. 9 and 10 show an air blower device for removing ablation plume, which may be used in the described is embodiment of the present invention. The air blower device is provided with a blower disposed internally in a portion indicated by number 26 and a mounting system for fixing the transparent plate 25, more specifically, a plate presser 27 for pressing the transparent plate 25 and a plate support 28 for supporting the same.

In the above air blower device, the plate presser 27 is fixed so that the aperture image of the diaphragm 13 is focused through the projection lens 14 on an upper surface of the transparent plate 25 to be disposed on the plate support 28, and then, the plate support 28 is moved down to hold the transparent plate 25 thereon. The transparent plate 25 is therefore fixedly held between the plate presser 27 and the plate support 28 being pressed upward, and the transparent plate 25 is ablated by the laser beam passing through an aperture 27a of the plate presser 27 so that a lens surface is provided on the surface. At the time of the ablation, the blower in the portion 26 blows toward the plate presser 27 to remove ablation plumes to be produced from the transparent plate 25.

By employing the above mentioned apparatus, the process of correcting the change of the ablation rate will be explained hereinafter.

Figure 7:
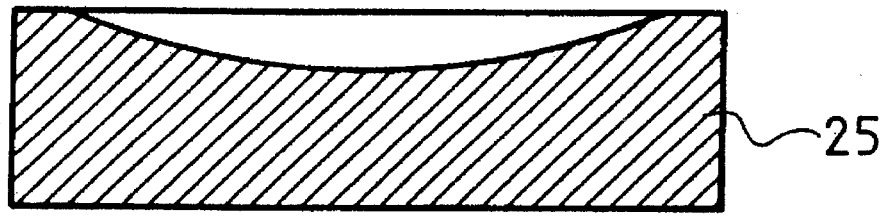
FIG. 7 is a schematic diagram showing an aspherical lens surface formed on a transparent plate 25 made from polymethyl metacrylate resin (PMMA)

Instead of the cornea 16, the transparent plate 25 made from polymethyl methacrylate resin (PMMA) is disposed at a position where the cornea 16 of the eye is to be disposed. The plane mirror 12 and the aperture 13 are controlled so that the transparent plate 25 is ablated, and an aspherical (or spherical) lens surface is formed on the transparent plate 25 as shown in FIG. 7. At the time of ablating, ablation plume produced from the ablation is removed by the air blower 23 in order to prevent the influence of ablation plume on the ablation rate.

Figure 8:
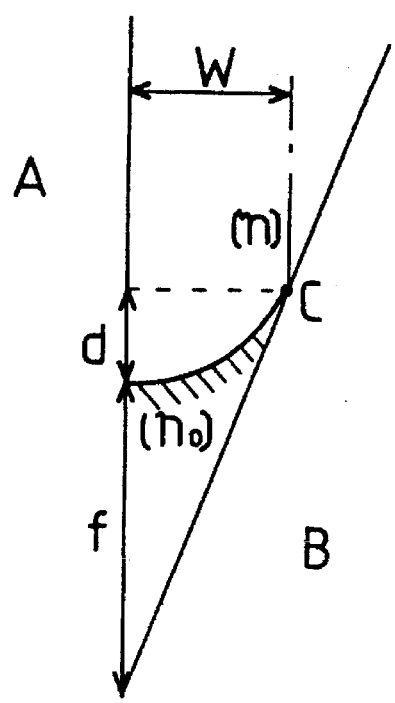
FIG. 8 is a diagram to explain the influence of change of ablation rate on the refractive power of eye to be ablated.

Assuming that a refractive index of medium A (air in here) is "n", and the same of medium B (PMMA in here) is "no", in general, the boundary between the mediums A and B may be aspherical lens surface as shown in FIG. 8, the depth "d" and the diameter "w" of any point C on the aspherical lens surface will satisfy the following relational formula (I). A mark "f" represents a focal distance. Strictly speaking, the boundary surface provided by the ablation apparatus in this embodiment is step-formed, but it approximates aspheric lens surface and therefore the refractive power of the lens surface can be measured also by lensmeters presently being sold.

$$w^2 = \{(n^2 - n_o^2)d^2 + 2n_o(n - n_o)fd\}/n_o^2 \tag{I}$$

When the depth "d" is increased by whole number times of ablation rate, and the diameter size of the aperture 13 is controlled so that the diameter "w" of projected image of the aperture in each ablation depth may satisfy the above formula (I), accordingly, the surface of the transparent plate 25 can be formed into lens surface.

If the ablation rate coincides with a reference value (designated value), a lens surface with an optional focal distance "f" can be freely produced only if the motion of the aperture 13 is controlled so as to satisfy the above formula (I). On the other hand, in a case where the transparent plate is processed as the actual ablation rate is out of the reference value, the change of the lens power of a produced lens can be found as follows.

If the above formula (I) is rewritten to another formula on lens power "D(1/f)", the following formula (II) will be provided;

$$D = \frac{2n_o(n-n_o)d}{n_o^2 W^2 - (n^2 - n_o^2)d^2} \quad \text{(II)}$$

wherein, if "w" is set to satisfactorily large numerical value as compared with "d", "$n_o^2 w^2$" is fully large in comparison with "$(n^2-n_o^2)d^2$" and accordingly approximates the following formula (III);

$$D = \frac{2n_o(n-n_o)}{n_o^2 W^2} d \quad \text{(III)}$$

therefore, the refractive power of the produced lens is proportional to the ablation depth "d". Namely, the change rate of the refractive power of lens coincides with the same of the ablation rate.

By measuring the refractive power of a simulated lens produced on the transparent plate 25 and comparing the measured value with the refractive power of lens to be formed at a reference ablation rate, it is possible to find the current ablation rate. The refractive power measured by the lensmeter 24 is input to the control device 19 via the input device 20. The control device 19 processes the change rate of the ablation rate based on the change rate of the refractive power of the lens. It is recognized that there is a regular relation between each ablation rate of the object to be processed and the transparent plate according to differences of materials of the object to be processed, i.e., kinds of animals.

Experiments on eyes of pig, rabbit and others by the present inventor have disclosed the result that ablation rates of those animals are about two or three times as large as the ablation rate of the transparent plate 25 made from polymethyl metacrylate resin (PMMA). It is therefore possible to find the current ablation rate to the object to be processed on the basis of the relation between the ablation rates of the object to be processed and the transparent plate 25 which are stored in the control device 19, and the change rate of the above processed ablation rate. It is generally possible to store the reference ablation rate of the processed object and simply multiply the reference ablation rate by the change of rate of lens power mentioned above.

As described above, when the current ablation rate is obtained, control of the apparatus is correct in accordance with the following methods.

The first correcting method is, in a case where the diameter of the aperture is represented as a function in regard to the ablated depth, to process a diameter of each aperture at whole number times of the current ablation rate and then control the aperture based on the processed result.

The second correcting method is, in a case of repeatedly emitting the laser pulse up to a regular depth, to divide the processing depth by the ablation rate and thereby determine the number of pulse to be repeatedly emitted. Of course, it is also possible to divide the number of pulse to be repeatedly emitted by the change rate.

The third correcting method is to adjust the output power of the laser based on the measured ablation rate, because the ablation rate can be made constant within a regular range according to the adjustment of the output power of the laser.

The present invention may be embodied in other specific forms without departing from the spirit or essential characteristics thereof. For instance, it is possible to use nontransparent material instead of transparent plate, and also to measure a reflection focal length by collimator and the like.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ablating apparatus, comprising:
   a controller;
   a laser beam source coupled to and governed by the controller;
   an optical system responsive to a laser beam from the laser beam source for directing the laser beam along a path to an ablation area position of a first object to be ablated;
   means disposed in the laser beam path responsive to the controller for changing the position of the ablation area of the first object to be ablated,
   a second object for positioning in the path of the laser beam, said second object having a known ablation rate relative to the first object to be ablated;
   first means coupled to the controller for instructing said ablation area position changing means and the laser source to ablate the second object by forming a curved surface having a first refractive power;
   means coupled to the controller for measuring the first refractive power of the curved surface of the second object to obtain a second measured refractive power; and
   means coupled to the measuring means for inputting the measured second refractive power to the controller said controller also including means for comparing the first refractive power to the second measured refractive power, and second means for controlling the laser source and the ablating area position changing means to ablate the first object by forming a curved surface based upon the comparison between the first and second refractive power.

2. An ablation apparatus according to claim 1, wherein the ablation area position changing means comprises a diaphragm with a variable aperture.

3. An ablation apparatus according to claim 1, wherein the measuring means includes a lensmeter for measuring the refractive powers.

4. An ablation apparatus according to claim 1, wherein the first object is a cornea and the second means is for changing curvature of said cornea.

5. An ablation apparatus according to claim 1, wherein the second object is transparent.

6. An ablation apparatus according to claim 5, wherein the second object is made from polymethyl metacrylate (PPMA).

7. A cornea operating apparatus for irradiating an eye to be ablated by a laser beam to correct a refractive error of the eye, the apparatus comprising:

a laser source for emitting a laser beam having a Gaussian distribution in a direction of beam cross section;

an optical system coupled to the laser source for irradiating the laser beam emitted from said laser source along a path and onto a surface of the cornea of the eye to be ablated;

scanning means positioned on the path of the optical system for scanning the laser beam in the direction of Gaussian distribution;

means coupled to a driving control means for determining an error in ablation rate between a refractive power of a simulated lens and a predetermined reference refractive power, the simulated lens being a reference object ablated by said optical system prior to and in place of the cornea of the eye being ablated; and said driving control means being governed by said determined error in the ablation rate for controlling output power of the laser beam emitted from the laser source and for controlling the scanning of the laser beam by said scanning means.

8. A cornea operating apparatus according to claim 7, wherein the means for determining the error in the ablation rate, comprises:

measuring means for measuring the refractive power of said simulated lens; and calculating means for calculating the error rate of the ablation rate based on the refractive power of the simulated lens measured by the measuring means and the predetermined reference refractive power.

9. A cornea operating apparatus according to claim 7, wherein said laser source comprises an excimer laser.

10. A cornea operating apparatus according to claim 7, wherein said reference object is made from transparent polymethyl metacrylate resin.

11. A cornea operating apparatus according to claim 7, further comprising ablation plume removing means for removing ablation plume while said reference object is being ablated, the ablation plume being produced from the ablation of the reference object during formation of the simulated lens.

12. A cornea operating apparatus according to claim 7, wherein the means for determining the error in the ablation rate, comprises:

measuring means for measuring the refractive power of said simulated lens; and calculating means for calculating the error rate of the ablation rate based on the refractive power of the simulated lens measured by the measuring means and the predetermined reference refractive power.

13. A cornea operating apparatus for irradiating an eye to be ablated by a laser beam to correct a refractive error of the eye, the apparatus comprising:

a laser source for emitting a laser beam along a path having a Gaussian distribution in a direction of beam cross section;

beam deflecting means along the path for deflecting a portion of the path of the laser beam emitted from the laser source;

scanning means in a portion of the laser path for scanning the deflected laser beam in the direction of Gaussian distribution;

means disposed in the laser beam path for changing a position of an ablation area on the cornea of the eye to be ablated by the laser beam;

means coupled to a driving control means for determining an error in ablation rate between a refractive power of simulated lens and a predetermined reference refractive power, the simulated lens being a reference object ablated by said optical system prior to and in place of the cornea of the eye being ablated; and said driving control means begin governed by the error of the ablation rate for controlling output power of the laser beam emitted from the laser source, the scanning of the laser beam and the position of the ablation area.

14. A cornea operating apparatus according to claim 13, further comprising ablation plume removing means for removing ablation plume while said reference object is being ablated, the ablation plume being produced from the ablation of the reference object during formation of the simulated lens.

15. A cornea operating apparatus according to claim 13, wherein said laser source comprises an excimer laser.

16. A cornea operating apparatus according to claim 13, wherein said ablated reference object is made from transparent polymethyl metacrylate resin.

17. A method for ablating to a desired shape an object to be processed positioned in an optical path of a laser beam, comprising the steps of:

positioning a rate reference object, having a known ablation rate, in the optical path of the laser beam;

forming on the rate reference object a curved surface based upon a first refractive power;

removing ablation plume produced by the rate reference object while being irradiated by the laser beam in order to maintain ablation stability;

measuring the formed curved surface to obtain a second refractive power;

comparing the first and second refractive powers;

calculating a rate of ablation for the object to be processed based on the comparison between the first and second refractive powers; and ablating the object to be processed based on the calculated ablation rate.

18. An ablating method according to claim 17, wherein the step of positioning the rate reference object, comprises positioning a transparent rate reference object.

19. An ablating method according to claim 17, wherein the step of removing the ablation plume comprises:

blowing air over the rate reference object while the object is being irradiated by the laser beam.

20. An ablating method according to claim 17, wherein the step comprises:

measuring the refractive power by a lensmeter.

21. A laser beam ablation method comprising the steps of:

ablating with the laser beam an ablation rate reference object to manufacture a simulated lens;

measuring a refractive power of the simulated lens;

calculating an error rate between the measured refractive power of the simulated lens and a predetermined reference refractive power;

calculating an ablation rate of an object to be ablated based on the calculated error rate of the refractive power; and ablating the object to be ablated by the laser beam based on the calculated ablation rate.

22. An ablating method according to claim 21, wherein said step of ablating with the laser beam an ablation rate reference object, comprises ablating an ablation rate reference object that includes transparent polymethyl methacrylate resin.

23. An ablating method according claim 21 wherein the step of ablating said object to be ablated includes ablating a cornea.

* * * * *